United States Patent [19]
Binder et al.

[11] Patent Number: 5,869,297
[45] Date of Patent: Feb. 9, 1999

[54] NANOFILTRATION PROCESS FOR MAKING DEXTROSE

[75] Inventors: Thomas P. Binder, N. Clinton; Donald K. Hadden; Lowell J. Sievers, both of Clinton, all of Iowa

[73] Assignee: Archer Daniels Midland Company, Decatur, Ill.

[21] Appl. No.: 896,154

[22] Filed: Jun. 10, 1992

Related U.S. Application Data

[63] Continuation-in-part of Ser. No. 498,344, Mar. 23, 1990, abandoned.

[51] Int. Cl.$^6$ ............................. C12P 19/02; C12P 19/04; B01D 61/00
[52] U.S. Cl. .......................... 435/105; 435/101; 210/651; 210/652; 210/654
[58] Field of Search .................................... 435/101, 105; 210/651, 652, 654

[56] References Cited

U.S. PATENT DOCUMENTS

| 4,429,122 | 1/1984 | Zupancic | 536/127 |
|---|---|---|---|
| 4,747,953 | 5/1988 | Zupancic et al. | 210/490 |

*Primary Examiner*—Francisco Prats
*Attorney, Agent, or Firm*—Laff, Whitesel, Conte & Saret, Ltd.

[57] ABSTRACT

A nanofilter membrane is used to filter the outflow of a food processing stream which begins with a starch slurry and ends with a glucose syrup which in its preferred form is about 95% dextrose and 5% di- and trisaccharides. The nanofilter membrane is able to pass the dextrose while retaining the di- and trisaccharides. As a result, the invention is able to produce substantially pure dextrose, with purity in a range which is well over 99%.

14 Claims, 3 Drawing Sheets

NANOFILTRATION PROCESS FOR MAKING DEXTROSE

This is a continuation-in-part of our application Ser. No. 07/498,344 filed Mar. 23, 1990, now abandoned.

This invention relates to a process of preparing high purity dextrose by nanofiltration—especially but not exclusively—for the production of dextrose.

Evaporation, freeze concentration, or freeze drying are common dewatering techniques used in the food, pharmaceutical and biological processing industries. Evaporation requires the input of about 1000 BTU for each pound of water that is evaporated (540 kcal/kg) while freezing requires about 144 BTU for each pound of water frozen, merely to effect the change in state of water from liquid to vapor or liquid to solid, respectively.

Since membrane filtration does not require a change in state to effect dewatering, it should result in considerable savings in energy. A less obvious advantage is the fact that no complicated heat transfer or heat-generating equipment is needed. Only electrical energy is required to drive a pump motor. Another advantage is that membrane filtration can be carried out at ambient or lower temperatures (e.g., to prevent microbial growth problems or denaturation of heat sensitive components) or at higher temperatures (e.g., to minimize microbial growth problems, to lower viscosity of the retentate thus lowering pumping costs, or to improve mass transfer). Since small molecules should normally pass freely through filtration membranes, their concentration on either side of the membrane should be about the same during processing and about equal to the original feed solution. Thus, membrane filtration offers many advantages over other dewatering processes.

A book entitled "Ultrafiltration Handbook" by Munir Cheryan, published by Technomics Publishing Co., Inc. 851 New Holland Ave., Lancaster, Pa. 17604 U.S.A. describes membrane filtration as a separation of two or more components from a fluid stream. A membrane is a selective barrier which prevents mass movement, but allows restricted or regulated passage, of one or more species through it. Membrane filtration includes the use of such a barrier to pass certain components while retaining certain other components of a mixture in order to separate dissolved solutes in liquid streams.

Membranes can be classified by their porous vs. nonporous structure. Osmosis involves a movement of a solvent from the dilute solution side through a semi-permeable membrane to the concentrated solution side of the membrane, responsive to the chemical potential difference between the water on either side of the membrane.

Five other major membrane separation processes are reverse osmosis, or ultrafiltration, microfiltration, dialysis and electrodialysis, which cover a wide range of particle sizes. Reverse osmosis or ultrafiltration permit a separation of dissolved molecules down to the ionic range. Reverse osmosis or hyperfiltration relates to dewatering while ultrafiltration simultaneously purifies, by concentrating, and fractionating macromolecules or fine colloidal suspension. Reverse osmosis or hyperfiltration retains most/nearly all components other than the solvent (water) itself, while ultrafiltration retains only the macromolecules or particles larger than about 10–200 Å. Ultrafiltration only needs a fairly low pressure for operation. Reverse osmosis, ultrafiltration, or hyperfiltration constitute continuous molecular separation processes which do not involve a phase change or interphase mass transfer, thus making these processes important for food, pharmaceutical and biological processing.

For these and other reasons, it is advantageous to use membrane filtration in the production of certain food products, such as dextrose. Heretofore, a drawback of using dextrose as a chemical feedstock centers about the difficulty encountered in obtaining a stream of dextrose with a sufficiently high purity. The dextrose molecules must be separated from molecules or other materials which have almost the same characteristics, such as maltose and higher oligosaccharides. The conventional process for producing a high purity dextrose (i.e. greater than 99% purity) requires a costly and time consuming crystallization of a very highly concentrated syrup. Therefore, a non-crystallization alternative process is needed to provide an inexpensive high purity dextrose stream.

Heretofore, membranes have not been able to separate closely similar materials. Diffusion through a reverse osmosis membrane is able to concentrate a stream containing dextrose, maltose, and salts in order to provide a purified aqueous stream. The reverse osmosis membrane does not separate the dextrose from the maltose and salts. While conventional ultrafiltration provides means for purifying or separating some fermentation and chemical products, it does not do very much toward separating and purifying fairly similar compounds, such as maltose and dextrose.

Accordingly, an object of the invention is to provide a process for preparing a second dextrose composition having a solids content of at least 99% dextrose comprising nanofiltering a first dextrose composition having a solids content of about 80 to 97% by weight dextrose and at least 2% of saccharides selected from the group consisting of disaccharides, trisaccharides and mixtures thereof; and recovering as the permeate said second dextrose containing a solids content of at least 99% dextrose.

Another object is to provide a nanofiltered dextrose composition having a dextrose solids content of at least 99%.

In keeping with an aspect of this invention, these and other objects are accomplished by providing a nanofiltration membrane at or near the output of a feed stream. The feed stream begins with a production of corn starch, proceeds through gelatinization, dextrinization, and saccharification steps to provide a feed stream of glucose syrup. The foregoing process may produce glucose syrup with a purity of about 95% dextrose, 5% di- and trisaccharides. The invention uses a nanofiltration process in order to further refine the syrup and remove most of the remaining 5% of non-dextrose materials. After the nanofiltration, the material may be considerably more than 99% pure dextrose.

Figure 1:
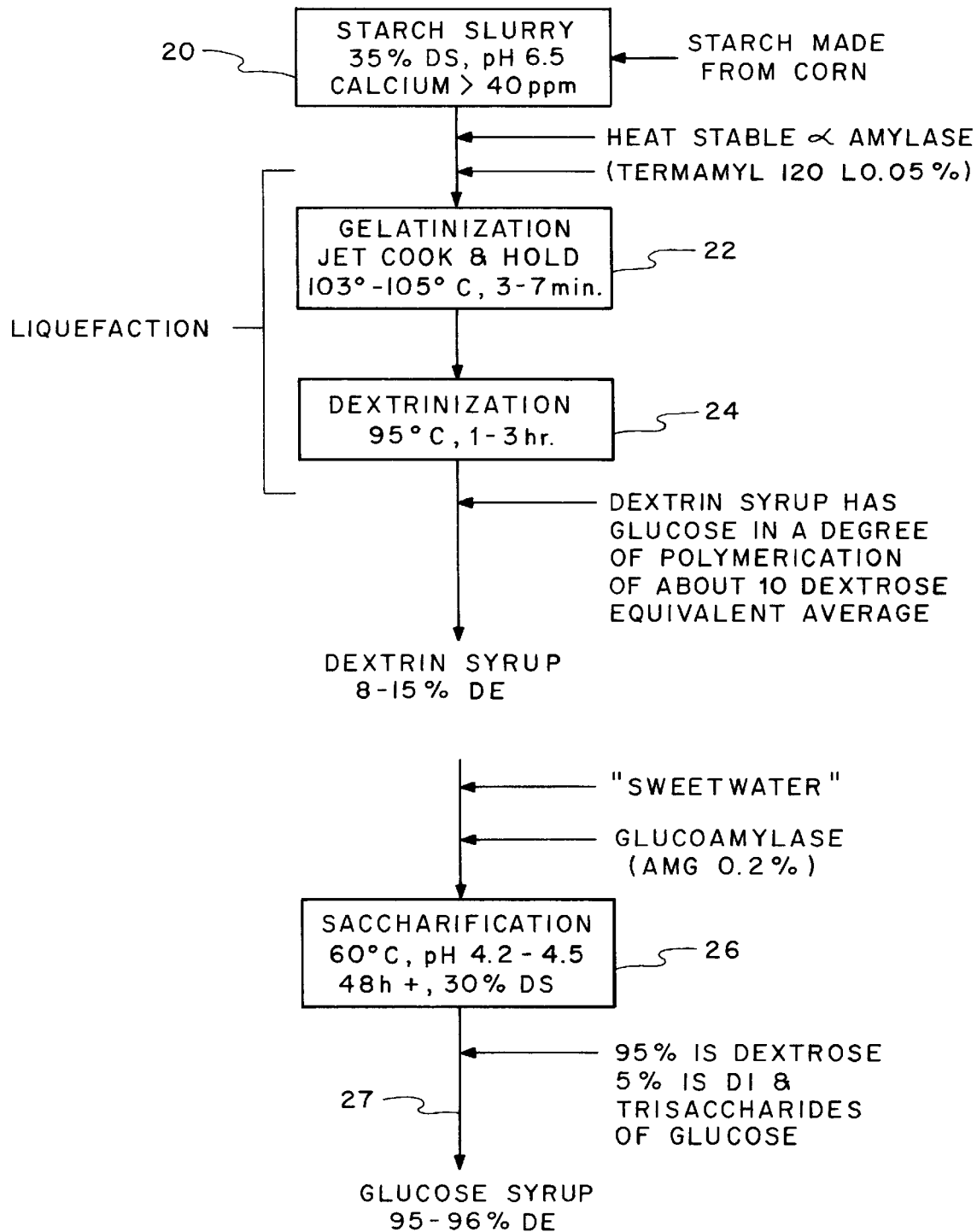
FIG. 1 shows known process steps for preparing a starting product for the present invention.

In our process of preparing a high purity dextrose, we nanofilter a glucose composition containing a mixture of dextrose, disaccharides and trisaccharides. Preferably, the glucose composition has a dextrose purity solids contact preferably of at least about 88% to produce a glucose composition having a dextrose purity solids content of at least 99%.

The nanofiltration uses a pressure driven membrane that is between reverse osmosis and ultrafiltration membranes, which is called a "nanofilter" membrane. The nanofiltration rejection is low for salts with monovalent anion and non-ionized organics with molecular weight below 150. Rejection is high for salts with di- and multivalent anions and organics with molecular weight about 300. When working with dilute streams of salts and sugars, these nanomembranes retain sugars and divalant ions versus monovalent ions.

However, in our process where we use a highly concentrated dextrose feed stream, these nanofilters yield an initial permeate dextrose feed stream which has a much higher purity than the original feed stream. Further work has also shown that when used in a downstream processing step these nanomembranes not only remove disaccharides and higher saccharides but also remove, to some extent, divalent salts thus providing a highly purified product.

The nanofilters we preferably use have a negative charge and rejects about 95% of components having a molecular weight of 500 or more. Also, the nanofilter preferably rejects about 5% of compounds having a molecular weight of 200 or less.

The nanofilters are operable at temperatures of less than 70° C., at pressures of less than 600 psig, have an operating pH range of 2 to 11, have a minimum solute rejection of $MgSO_4$ of 95%; a glucose (molecular weight 180) rejection of about 90 to about 99+%; a lactose (molecular weight 340) and sucrose (molecular weight 342) rejection of at least 97% and preferably 98% to about 99+%.

The specific nanofilters we have used are described hereinafter.

Presently FilmTec, a company located at 7200 Ohms Lane, Minneapolis, Minn. 55435, has two acceptable nanofiltration membranes, NF70 and NF40 (NF stands for nanofiltration). Each membrane has a negative surface charge which has not been quantified.

The nanofilters NF70 and NF40 are crosslinked aromatic polyamides. The filter membranes NF40 and NF70 are similar; however, the membrane NF40 has a slightly lower NaCl rejection, which indicates that its pores are slightly larger than the pores of the NF70 membrane.

By way of example, FilmTec describes their nanofiltration membrane NF70, as follows:

GENERAL SPECIFICATIONS

Configuration Spiral Wound

Pressure Range: 70–300 psig pH Range: 2–11 (1–12 short term)

Max. Feed Temp*: 70° C.

Chlorine Tolerance: 1,000 ppm-hours (approx.)

*NOTE: Not recommended to exceed maximum operating temperature due to breakdown of materials at high temperatures.

ELEMENT SPECIFICATIONS: Specifications are based on 1,000 mg/l solute feed solution at 70 psig net pressure, 25° C., 10% recovery, pH 5–8.

| MODEL | PERM. RATE GPD | MIN. SOLUTE REJECTION MgSO4 |
| --- | --- | --- |
| M-N2540F70 | 600 | 96% |
| M-N4040F70 | 1800 | 96% |
| M-N8040F70 | 7500 | 96% |

PERFORMANCE DATA

INORGANICS: The following data is based on 70 psig net pressure, 25° C., 10% recovery, pH 7–8, inorganic rejections may vary with concentration.

| CONSTITUENT | UNITS | TAPWATER % REJECTION |
| --- | --- | --- |
| Sodium chloride | mg/l | 80% |

ORGANICS: The following data is based on 70 psig net pressure, 25° C. and 10% recovery.

| CONSTITUENT | MOLECULAR WT. | % REJ. |
| --- | --- | --- |
| Glucose | 180 | 98% |
| Sucrose | 342 | 98% |
| Lactose | 340 | 98% |

The filmtech membrane NF40 is described as:

GENERAL SPECIFICATIONS

Configuration Spiral Wound

Pressure Range: 70–400 psig pH Range: 2–11

Max. Feed Temp: 50° C.

Chlorine Tolerance: 2,000 ppm-hours (approx.)

ELEMENT SPECIFICATIONS: Specifications are based on 1,000 mg/l solute feed solution at 70 PSI net pressure, 25° C., 10% recovery, pH 5–8.

| MODEL | PERM. RATE GPD | MIN. SOLUTE REJECTION MgSO4 |
| --- | --- | --- |
| M-N2540D | 600 | 96% |
| M-N4040D | 1650 | 96% |
| M-N8040D | 6500 | 96% |

PERFORMANCE DATA

INORGANICS: The following data is based on 100 psig net pressure, 25° C., 10% recovery, pH 7–8, inorganic rejections may vary with concentration.

| CONSTITUENT | UNITS | TAPWATER % REJECTION |
| --- | --- | --- |
| Bicarbonate | mg/l | 78% |
| Chloride | mg/l | 50% |
| Calcium | mg/l | 90% |
| Magnesium | mg/l | 92% |

ORGANICS: The following data is based on 100 psig net pressure 25° C. and 10% recovery.

| CONSTITUENT | % FEED CARE | MOLECULAR WT. | % REJ. |
| --- | --- | --- | --- |
| Fructose | 10.0 | 180 | 99+ |
| Sucrose | 10.0 | 342 | 99+ |
| Lactose | 6.2 | 340 | 99+ |

Some of the operating conditions and performances of the FilmTec nanofilter membranes are shown in Table 1.

TABLE 1

OPERATING CONDITIONS AND PERFORMANCE FOR FILMTEC NF MEMBRANES

|  | NF70 | NF40 |
|---|---|---|
| pressure to produce |  |  |
| 43 l/m²/h permeate flux*, bar | 6 | 20 |
| Operating pH range | 3–9 | 2–10 |
| Max. Temp. °C. | 70° C. | 70° C. |
| Approximate solute Rejection** |  |  |
| NaCl | 70 | 45 |
| MgSO$_4$ | 98 | 95 |
| Glucose (MW 180) | 98 | 90 |
| Sucrose (MW 342) | 99 | 98 |

*at 25° and 0.2% MgSO$_4$
**at 25° and 0.2% solute concentrations

Another source of nanofiltration membranes is Filtration Engineering Co. Inc. 4974 County Road 18 North, New Hope, Minn. 55428. Filtration Engineering describes its FE-700-002 membrane as a cross-linked polyamide, having a rejection characteristics which enables it to discriminate among low molecular weight species. This membrane has rejection characteristics which are between those common in reverse osmosis and ultrafiltration. The pore structure of the membrane enables a separation between sodium chloride and calcium sulfate. The utility of the membrane is said to be further enhanced by the simultaneous ability to concentrate the retained species. This membrane gives the users considerable latitude in process stream parameters, such as variations of pH, ionic strength, and temperature.

The manufacturer describes the Thin Film FE-700-002 membrane characteristics, as follows:

Composition: Crosslinked Polyamide
Permeability: (Nominal)

| NaCl | 95% |
|---|---|
| Lactose | 0–4% |
| Magnesium Sulfate |  |
| Calcium Chloride | 70% |
| Calcium Phosphate | 20–60% (pH Dependent) |
| Citric Acid | 10–95% (pH Dependent) |
| Acetic Acid | 10–95% (pH Dependent) |

Molecular Weight Rejections:

| Rejection above 500 | 95% |
|---|---|
| Rejection Below 200 | 5% |

Flux Rate: 20 l/m²/h nominal design flux rate 40° C.
Membrane size: 4"×30" spiral with 6 m² membrane area per element
Operating Pressure: 41 Bar (600 psig) Max. 30–40 Bar (450–600 psig) recommended.
Temperature limitations: 60° C. Maximum, 10°–50° C. recommended.
pH Tolerance 2.3 minimum 11.0 maximum short term exposure 2.3 to 10.0 recommended
Oxidizer tolerance: NONE
Rejection rate: >99% True Protein (TRP)
Flux rate: 27 l/m²/h nominal design flux rate (50° C.)
Additional thin film membranes which are useful for our process and system is TFM L type Desal-5 thin film elements sold by Desalination Systems, Inc. of Escondido, Calif. 92028. Desalination Systems describes their TFM membranes as having a 200–300 molecular weight cut-off, has an operating range of 70–400 psig with a maximum pressure of 600 psig. The operating pH range is 2–11; the cleaning pH range is 2–11.5; and the cholorine tolerance is 2000 ppm-hours. The membranes have a fructose rejection of 99% and sodium chloride rejection of 50% based on a 2% solute at 1000 psig net pressure. With regard to Magnesium sulfate there is a 96% rejection at 1000 ppm solute at 100 psig net pressure.

The data for three of Desalination Systems, Inc. filters based on 1000 ppm MgSO$_4$ solution at 100 psig net 25° C. and 10% recovery. Individual element flux may vary ±15%.

|  | Flux |  | Min. |
|---|---|---|---|
| Model | GPD | M3/D | Rej. % |
| DL4026F | 2200 | 8.33 | 96 |
| DL4040F | 3300 | 12.50 | 96 |
| DL8040F | 13,000 | 49.24 | 96 |

A company Osmonics Inc. manufactures an experimental membrane designated "Osmo MX-06" which is a thin film, membrane similar to the Filtration Engineering membranes. However, the manufacturer has not published any specifications on this membrane.

For all the nanofilter membranes, the rejection of magnesium sulfate is fairly high (90–98 percent), while the rejection of sodium chloride is generally in the 50 percent range or lower. Since these membranes are negatively charged, it is the anion repulsion which mainly determines the solute rejection. For example, the rejection of calcium chloride is about the same (can even be lower), than that of sodium chloride while rejection of sodium sulfate is about the same as that for magnesium sulfate. Di- and multivalent anions are highly rejected. So far, no known case has evolved where highly charged cations have interacted with the nanofiltration membranes to give a positive net surface charge.

In general, according to the invention, a glucose having a dextrose purity solids content of at least 88.0% and a dissolved solids content of 5.0 to 50% is fed to a nanofilter under pressure and below 70° C. The product passes through the membrane while varying degrees of the larger molecules do not pass through and are retained by the membrane. The amount of any given molecule passing through the membrane depends on the molecular weight, ionic charge, and concentration of the molecule in the feed stream.

During an experimental practice of the invention, dextrose was retained by the membrane in a low concentration; however, when a 28% dextrose is used, the dextrose permeates to some extent while virtually all of the higher oligosaccharides are retained.

In the case of an organic acid salt, such as lactic acid more or less of the acid appears in the permeate stream depending on whether it is present as salt or as a free acid. The stream permeates the membrane faster as the free acid than it does as the salt.

One of the starting compositions is prepared by the steps outlined in FIG. 1. This is a known procedure for preparing a glucose composition having a high dextrose purity. This process is described and the schematic of this process is taken from the *Novo Handbook of Practical Biotechnology*, which is published by Novo Industries, A/S Enzyme Division, Boysuard, Denmark.

A purified cornstarch slurry 20, having a calcium content of greater than 40 ppm and 35% by weight dissolved solids content and a pH of 6.5, is pretreated to provide a preliminary dextrose conversion. The starch slurry is mixed with the enzyme known as α amylose termamyl L120 to a concentration of 0.05%. The starch and α-amylose enzyme are jet cooked at 103°–105° C. for 3–7 minutes to form a gelatin 22. The gelatin is then cooled and maintained at a temperature of about 95° C. for about 1–3 hours, 24 to form a dextrin syrup having a glucose degree of polymerization of 8 to 15% dextrose equivalent.

The dextrin syrup is diluted with sweetwater (generally dextrose water) and the pH is adjusted to about 4.2–4.5. Glucoamylose (AMG 0.2%) is added to the diluted dextrin syrup. The diluted dextrin syrup and glucoamylose are maintained at approximately 60° C. for about 48 hours, at a pH of 4.2 to 4.5 step 26 to hydrolyze the dextrin to dextrose units. The glucose syrup 27 recovered has a dextrose equivalent of about 95 to 96% and 4 to 5% di-tri-saccharides.

The above process is one process of preparing the starting product of our process. Glucose syrups produced from other process may also be utilized.

Figure 4:
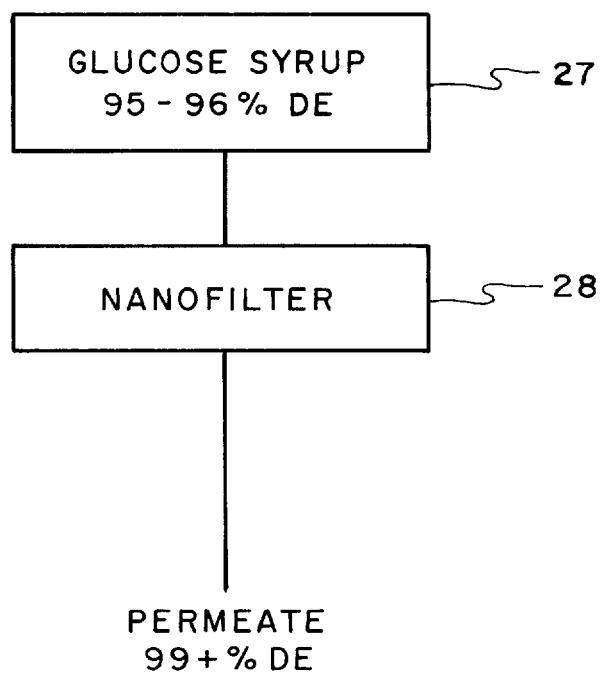
FIG. 4 is a flow chart of FIG. 1 and incorporates our invention.

Referring to FIG. 4, the glucose syrup 27 is then subjected to nanofiltration by use of a nanofilter membrane 28.

The glucose syrup which we subject to nanofiltration has a dissolved solids content of about 5% to about 50% with the dissolved solids having a dextrose content of from about 80% to about 97% and preferably about 85% to about 96% with at least about 2% di-and trisaccharides. The most preferred is a dextrose content of about 88–96%. Generally, the percentage of di-and trisaccharides are higher.

Figure 2:
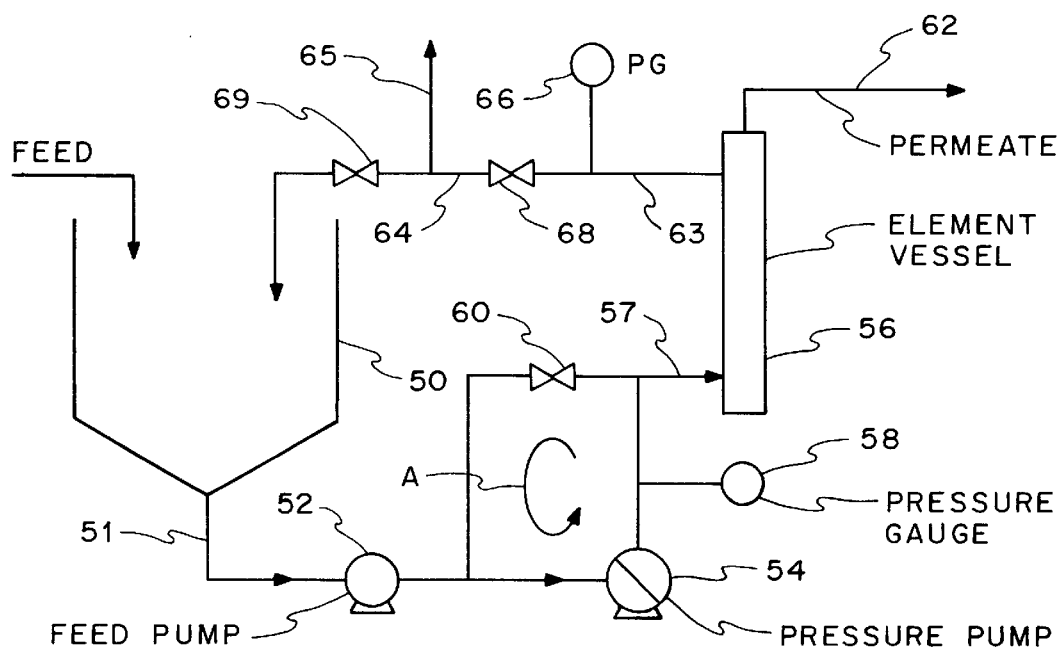
FIG. 2 is a flow diagram which shows a system designated "Osmo 19T" by its manufacturer Osmonics Inc. of Minnetonka, Minn. that was used to conduct tests leading to some working examples.

FIG. 2 shows a laboratory instrument which has been designated "Osmo 19T" by its manufacturer. This instrument was used in the laboratory to make experimental runs leading to some of the following working examples. It has an open tank 50 for holding glucose syrup 27, the tank being coupled through a feed pump 52 and a pressure pump 54, to a pressure membrane vessel 56. A pressure gauge 58 maintains about 450 psig at 4–5 gallons per minute. Suitable valve means 60 passes a limited flow which creates a feed back loop represented by arrow A in order to mix some of the feed stream which has gone through the turbulence of pump 54 back into the fresh, incoming feed stream. The limited flow also buffer stores some material to adjust the line pressure to the 450 psig.

The pressure membrane vessel 56 may be thought of as a stainless steel tube preferably having a plurality of spiral wound membranes in its interior. The entrance and exit chambers with the only passage between them being via the membranes. The interior of the pressure vessel is arranged to permit only the permeate to exit through line 62 and the retentate to exit through line 63. The feed 51 in the preferred embodiment contains a solids content of 85% to 96% dextrose and over 2% di- and trisaccharides the feed 51 enters vessel 56 via entrance line 54 on an entrance side of the membranes. The feed is nonfiltered by the membranes. On one side of the membranes the permeate passes and leaves from an exit side 62.

The permeate at 62 was about 99+% dextrose solids content and is considered almost pure dextrose. Therefore, on the entrance side of the membrane, material which does not pass through the membrane builds up and could accumulate to clog the membrane. To avoid this clogging, most of the retentate is removed by line 65 by cleaning the membranes. Some of the "retentate" is recycled via line 67 to the feed tank 50. A pressure gauge 66 is set at about 430 psig which establishes a net difference of about 20 psig across the membranes. The valves 68 and 69 are set to adjust the volume of the fed back retentate.

Figure 3:
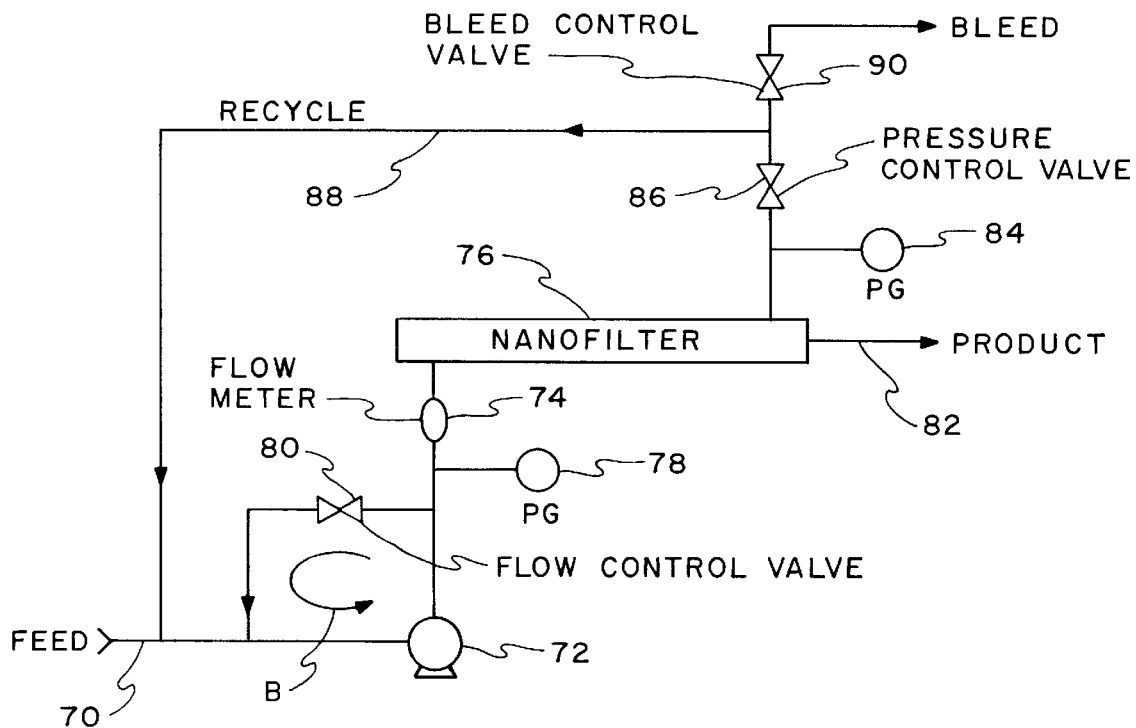
FIG. 3 is a flow chart of a pilot system used in a plant which practices the invention in order to produce other working examples.

A pilot system (FIG. 3) was set up in a factory to test larger scale production. In this example, the glucose syrup 27 enters via a feed pipe 70, passed through a pump 72, and flow meter 74 to a pressure nanofilter vessel 76, which is constructed approximately the same as the vessel 56. A pressure gauge 78 controls the input pressure to the nanofilter. A feed recirculation loop (shown by arrow B) has a flow which is controlled by valve 80.

The permeate product of the purified dextrose product is recovered via product line 82. A pressure gauge 84 maintains the back pressure on the membranes in the nanofilter in about the same manner that gauge 66 maintains it. Pressure control valve 86 is adjusted to maintain the desired pressure reading at gauge 84. A portion of the retentate is recycled via line 88 to the input of pump 72. The valve 90 is set so that a percentage of the retentate is bled off. This bleed material may be utilized in any suitable manner, as by returning to some appropriate upstream point in the process of FIG. 1 or by using it to produce products other than substantially pure dextrose.

EXAMPLE 1

Three membranes were tested for dextrose purification of a feed stream derived from saccharified corn starch, using an Osmo 19T pilot system.

| Membrane | Recirc Flow gpm | °C. Temp. | Permeate Flow gph | GF²D | Pressure PSI In | Pressure PSI Out |
|---|---|---|---|---|---|---|
| Exp. M. Series | 3 | 56 | 3.5 | 5.6 | 370 | 350 |
| Filmtec NF-40 | 3 | 46 | 2.0 | 2.2 | 370 | 340 |
| Filtration Eng. UO (Desal-5) | 3 | 45 | <1 | | 450 | 410 |

Results

| | Dextrose Concentration g/100 ml | | % Dextrose Purity | |
|---|---|---|---|---|
| | Feed | Permeate | Feed | permeate |
| Exp. M. Series | 29.8 | 21.3 | 96 | 99.7 |
| NF-40 | 30 | 23 | 96.1 | 99.2 |
| FE UO | 30 | 19.7 | 96.2 | 98.8 |

EXAMPLE 2

Larger scale runs were carried out using a Filtration Engineering UO membrane. An around the clock system was set up to determine filtration during a production scale of operations. The membrane had 1000 square feet of filtration area. The results are shown below:

| Pressure PSI | | Flow gpm | | | | Dextrose |
|---|---|---|---|---|---|---|
| Time | In | Out | Recirc. | Bleed | Product | Temp. F° | Purity |
| 0700 | 410 | 380 | 121 | 10 | 2.4 | 136 | 99.7 |
| 0900 | 410 | 379 | 122 | 10 | 2.5 | 138 | |
| 1100 | 410 | 380 | 121 | 9 | 2.5 | 138 | 99.6 |

-continued

| Pressure PSI | | Flow gpm | | | | Dextrose |
|---|---|---|---|---|---|---|
| Time | In | Out | Recirc. | Bleed | Product | Temp. F° | Purity |
| 1300 | 410 | 379 | 120 | 10 | 2.4 | 137 | |
| 1700 | 410 | 382 | 120 | 10 | 2.5 | 143 | |
| 1900 | 410 | 399 | 120 | 11 | 2.2 | 143 | 99.7 |
| 2100 | 410 | 381 | 121 | 10 | 2.4 | 139 | |
| 2300 | 410 | 379 | 119 | 9 | 2.2 | 136 | 99.7 |
| 0100 | 410 | 382 | 121 | 9 | 2.3 | 138 | |
| 0500 | 410 | 381 | 122 | 10 | 2.3 | 136 | 99.6 |
| 0500 | 410 | 378 | 120 | 9 | 2.4 | 136 | |

The daily average results for the product and feed properties are shown below.

| | Dry Solids w/w | Dextrose Purity % |
|---|---|---|
| Feed | 27.2 | 96.8 |
| Product | 19.8 | 99.7 |
| Bleed* | 28.7 | 96.0 |

* When the membrane passes certain material and blocks other material, the blocked material builds up a concentrated solution on one side of the membrane. A certain percentage of this concentrated solution must be withdrawn before the concentration becomes excessive. That drawn off material is called "bleed".

EXAMPLE 3

Twenty gallon batches of dextrose liquor having different percentages of dry solids were processed in an Osmo 19T pilot system, using a Filmtech NF-40 membrane. The process conditions, fluxes and purity of feed and product streams are shown below.

| DEXTROSE FEED | | | | DEXTROSE PRODUCT | | | | Recom Flow GPH | Temp °C. | Permeate Flow GPM | GF²D | Pressure In | Pressure Out | Volume Permeated For Composite Product Sample |
|---|---|---|---|---|---|---|---|---|---|---|---|---|---|---|
| % Total Dry Solids | DP3 | DP2 | DP1 | % Total Dry Solids | DP3 | DP2 | DP1 | | | | | | | |
| 51 | 1.2 | 3.5 | 95.3 | 45.6 | 0 | 0.4 | 99.6 | 4 | 58 | 1.5 | 1.8 | 480 | 450 | 9.4 L |
| 41.6 | 1.5 | 4.1 | 94.4 | 37.4 | 0.1 | 0.3 | 99.6 | 4 | 58 | 1.5 | 1.8 | 470 | 440 | 11 L |
| 33.6 | 1.9 | 5.0 | 93.1 | 30.7 | 0.0 | 0.4 | 99.6 | 4 | 57 | 1.25 | 1.5 | 470 | 450 | 12 L |
| 20.9 | 2.0 | 6.6 | 91.4 | 13.4 | 0.0 | 0.4 | 99.6 | 4 | 53 | 2 | 2.4 | 410 | 385 | 19 L |
| 10.5 | 2.2 | 8.9 | 88.9 | 3.4 | 0.0 | 0.3 | 99.7 | 4 | 54 | 7 | 8.4 | 310 | 275 | 19 L |

EXAMPLE 4

Results from the same system that was used as in Example 2 after five days.

| Pressure PSI | | | Flow gpm | | | | Dextrose |
|---|---|---|---|---|---|---|---|
| Time | In | Out | Recirc. | Bleed | Product | Temp. °F. | Purity |
| 0700 | 410 | 382 | 121 | 9 | 2.8 | 154 | 99.3 |
| 1100 | 410 | 383 | 120 | 9 | 2.8 | 154 | 99.4 |
| 1500 | 410 | 381 | 120 | 8 | 3 | 155 | 99.6 |
| 1900 | 410 | 380 | 122 | 8 | 3.2 | 155 | 99.7 |
| 2300 | 410 | 379 | 122 | 8 | 3.3 | 155 | 99.8 |
| 0300 | 410 | 383 | 121 | 8 | 3.4 | 156 | 99.7 |

Average for the day.

| | Dry Solids W/W | Dextrose Purity % |
|---|---|---|
| Feed | 28.4 | 96.2 |
| Product | 22.1 | 99.6 |
| Bleed | 30.5 | 95.1 |

EXAMPLE 5

A concentrated 500,000 MW ultrafiltered *Lactobacillus casei* fermentation broth which contained approximately 36% lactate ion was diluted to approximately 10% lactate, ultrafiltered (50,000 insert, MW) and nanofiltered at pH 6.0 and at pH 2.3 after pH adjustment with sulfuric acid. The fermentation broth used in this Example 5 was taken from a 48-hour fermentation of a solution containing 140 grams of dextrose per liter, 5 grams/liter of yeast extract, 30 grams steepwater dry solids/liter, and 1.0 grams of $(NH_4)_2PO_4$ per liter. This mash was fermented with *Lactobacillus casei* subspecies *rhamnosus* with ammonia added for pH control at pH 6.0 and 110° C. When all of the dextrose was fermented, the broth was ultrafiltered and concentrated to 36% lactate ion.

For this example, testing was conducted on an Osmo 19T pilot system with an Osmo MX06 membrane at approximately 400 PSI and 45° C. Samples of the ultrafiltered material (A), nanofiltered at pH 6 (B), and nanofiltered at pH 2.3 (C) were all adjusted to pH 2.4 and concentrated to between 20–30% lactic acid for further processing. An HPLC (high pressure liquid chromatography) analysis was carried out on these samples with the results which are shown below.

| | % Total Dry Solids | | | |
|---|---|---|---|---|
| Sample | % $DP_3$ + Salts | % $DP_2$ | % $DP_1$ | Lactic Acid |
| A | 34 | 2.2 | 1.6 | 60 |
| B | 34 | 0.17 | 0.6 | 62 |
| C | 29 | 0.08 | 0.5 | 69 |

$DP_3$ + = Trisaccharides and higher polymers.
$DP_2$ = Disaccharides
$DP_1$ = Monosaccharides As can be seen the nanofilter removed most of the disaccharides and some of the monosaccharides. Also, at pH's where the lactic acid is not ionized, the ratio of lactic acid to inorganic salts in the permeate increased, thereby providing a higher purification factor.

Those who are skilled in the art will readily perceive how to modify the invention. Therefore, the appended claims are to be construed to cover all equivalent structures which fall within the true scope and spirit of the invention.

The claimed invention is:

1. A process for preparing a second dextrose composition having a solids content of at least 99% dextrose comprising
nanofiltering a first dextrose composition having a solids content of about 80 to 97% by weight dextrose and at least 2% of saccharides selected from the group consisting of di-saccharides, trisaccharides and mixtures thereof; and
recovering as the permeate said second dextrose containing a solids content of at least 99% dextrose.

2. The process of claim 1 wherein said first dextrose composition has a solids content of 85 to 96% by weight dextrose.

3. The process of claim 1 comprising maintaining the pressure of said nanofiltering step in the range of 400 to 450 psig and at a temperature in the range of 50° F. to 70° F.

4. The process of claim 1 comprising nanofiltering said first dextrose composition with a negatively charged polyamide nanofilter which has a pressure range of 70–300 psig, a pH range of 2–11, a maximum feed temperature of 70° C., a minimum $MgSO_4$ solute rejection of 96% based on 1000 mg/l solute feed solution at 70 psig net pressure and 25° C. and pH of 5–8 and 10% recovery;
and a glucose, sucrose and lactose rejection of at least 97% based on 70 psig net pressure, 25° C. and 10% recovery.

5. The process of claim 1 comprising nanofiltering said first dextrose composition with a negatively charged polyamide nanofilter which has a pressure range of 70–300 psig, a pH range of 2–11, a maximum feed temperature of 70° C., a minimum $MgSO_4$ solute rejection of 96% based on 1000 mg/l solute feed solution at 70 psig net pressure and 25° C. and pH of 5–8 and 10% recovery;
and a glucose, sucrose and lactose rejection of at least 99% based on 100 psig net pressure, 25° C. and 10% recovery.

6. The process of claim 1 comprising nanofiltering said first dextrose composition with a negatively charged nanofilter which has a pressure range of up to 600 psig, a pH range of 2–11, a 200–300 molecular weight cut-off.

7. The process of claim 1 comprising
feeding said first dextrose composition to a negatively charged nanofilter at a pressure of 100 to 500 psig and at a temperature of 100° F. to 160° F.

8. The process of claim 7 wherein said first dextrose composition has dissolved solids content of 5 to 50% and 88 to 96% dextrose.

9. The process of claim 1 which includes preparing said first dextrose composition from a corn starch slurry which is first gelatinized then dextrinized, then saccharified.

10. The process of claim 2 which includes preparing said first dextrose composition from a corn starch slurry which is first gelatinized then dextrinized, then saccharified.

11. The process of claim 6 which includes preparing said first dextrose composition from a corn starch slurry which is first gelatinized then dextrinized, then saccharified.

12. The process of claim 9 wherein said corn starch is gelatinized for 3 to 7 minutes, dextrinized for 1 to 3 hours and saccharified for at least 36 hours.

13. The process of claim 10 wherein said corn starch is gelatinized for 3 to 7 minutes, dextrinized for 1 to 3 hours and saccharified for at least 36 hours.

14. The process of claim 11 wherein said corn starch is gelatinized for 3 to 7 minutes, dextrinized for 1 to 3 hours and saccharified for at least 36 hours.

* * * * *